United States Patent
Nagai

(10) Patent No.: US 10,475,953 B2
(45) Date of Patent: Nov. 12, 2019

(54) OPTICAL ANALYZER AND METHOD FOR PRODUCING THE SAME

(71) Applicant: SHIMADZU CORPORATION, Kyoto-shi, Kyoto (JP)

(72) Inventor: Yusuke Nagai, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/567,679

(22) PCT Filed: Apr. 24, 2015

(86) PCT No.: PCT/JP2015/062486
§ 371 (c)(1),
(2) Date: Oct. 19, 2017

(87) PCT Pub. No.: WO2016/170670
PCT Pub. Date: Oct. 27, 2016

(65) Prior Publication Data
US 2018/0166605 A1   Jun. 14, 2018

(51) Int. Cl.
*G01N 21/00*   (2006.01)
*H01L 33/00*   (2010.01)
(Continued)

(52) U.S. Cl.
CPC ......... *H01L 33/0075* (2013.01); *G01N 21/05* (2013.01); *G01N 21/59* (2013.01);
(Continued)

(58) Field of Classification Search
CPC .......... G01N 2021/6469; G01N 21/05; G01N 21/255; G01N 21/59; G01N 2201/062;
(Continued)

(56) References Cited

U.S. PATENT DOCUMENTS 6,197,503 B1 * 3/2001 Vo-Dinh .............. B01J 19/0046
435/183
8,213,015 B2   7/2012 Kraizcek et al.
(Continued)

FOREIGN PATENT DOCUMENTS

EP   2 196 796 A1   6/2010
JP   1-97841 A   4/1989
(Continued)

OTHER PUBLICATIONS

International Search Report dated Jul. 21, 2015, issued in counterpart of International Application No. PCT/JP2015/062486 (2 pages).
(Continued)

*Primary Examiner* — Sunghee Y Gray
(74) *Attorney, Agent, or Firm* — Westerman, Hattori, Daniels & Adrian, LLP

(57) ABSTRACT

A passage (3) for a sample solution is formed in a sapphire base body (2) used as a substrate for semiconductor devices. An LED (4) and a photodiode (5) are formed on the base body (2) by a semiconductor manufacturing process so that they face each other across the passage (3). The LED (4) emits light into the base body (2). This light is transmitted through the sample solution in the passage (3), undergoing absorption according to the concentration and other properties of the solution. The transmitted light passes through the base body (2) and reaches the photodiode (5), producing a detection signal corresponding to the incident light amount. Since the light source and photodetector are integrated with the base body (2) serving as a flow cell, the present device is small and lightweight. Furthermore, no cumbersome task of aligning optical axes in the device-assembling process is needed.

6 Claims, 2 Drawing Sheets

(51) Int. Cl.
*G01N 21/05* (2006.01)
*G01N 21/59* (2006.01)
*G01N 35/08* (2006.01)
*H01L 31/18* (2006.01)
*G01N 21/25* (2006.01)
*G01N 21/64* (2006.01)
*H01L 25/16* (2006.01)

(52) U.S. Cl.
CPC ......... *G01N 35/08* (2013.01); *H01L 31/1828* (2013.01); *G01N 21/255* (2013.01); *G01N 2021/6469* (2013.01); *G01N 2201/062* (2013.01); *H01L 25/167* (2013.01)

(58) Field of Classification Search
CPC .. G01N 35/08; H01L 31/1828; H01L 33/0075
USPC ........................................................ 356/432
See application file for complete search history.

(56) References Cited

U.S. PATENT DOCUMENTS

| | | | |
|---|---|---|---|
| 9,643,181 B1* | 5/2017 | Chang | ............... B01L 3/502715 |
| 2004/0115861 A1 | 6/2004 | Wong et al. | |
| 2004/0223159 A1 | 11/2004 | Iwata et al. | |
| 2006/0119843 A1 | 6/2006 | O'Connell | |
| 2008/0197272 A1 | 8/2008 | Kiesel et al. | |
| 2010/0276665 A1* | 11/2010 | Wang | ................... H01L 21/0237 257/15 |
| 2011/0249259 A1 | 10/2011 | Van Dorpe et al. | |
| 2011/0262307 A1* | 10/2011 | Packirisamy | .......... G01N 21/05 422/82.08 |
| 2013/0161797 A1* | 6/2013 | Aida | ...................... C30B 33/04 257/622 |
| 2014/0262783 A1* | 9/2014 | Chang | ............. G01N 27/44721 204/452 |
| 2016/0197225 A1* | 7/2016 | Payne | ..................... H01L 31/18 438/57 |

FOREIGN PATENT DOCUMENTS

| | | |
|---|---|---|
| JP | 2004-198420 A | 7/2004 |
| JP | 2004-219401 A | 8/2004 |
| JP | 2011-237384 A | 11/2011 |
| JP | 2012-511705 A | 5/2012 |
| JP | 2012-194020 A | 10/2012 |
| WO | 2010/066795 A2 | 6/2010 |

OTHER PUBLICATIONS

Office Action dated Jul. 22, 2019, issued in counterpart CN Application No. 201580079131.6, with English translation (16 pages).

* cited by examiner

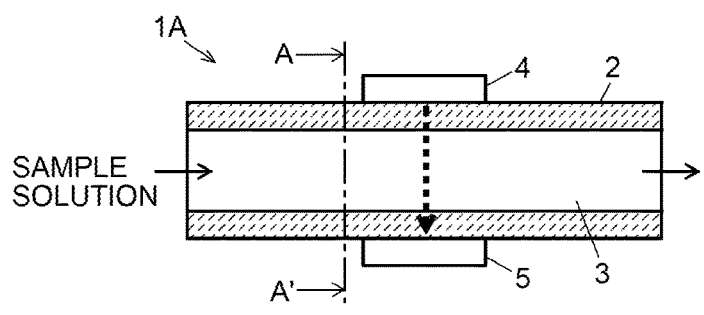
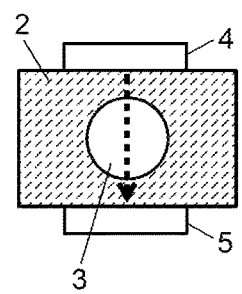
Fig. 1A    Fig. 1B
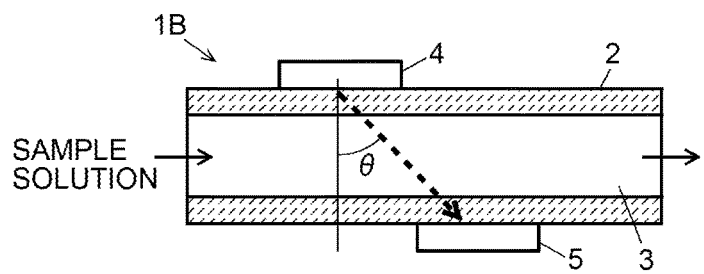
Fig. 2
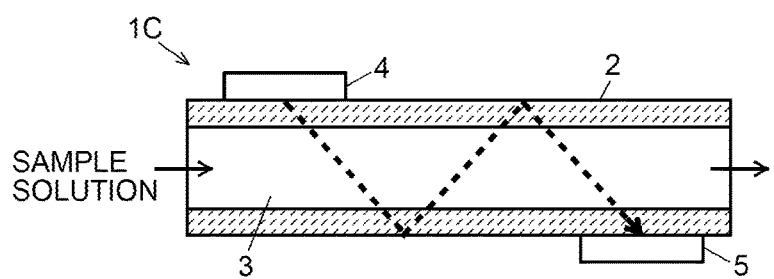
Fig. 3

OPTICAL ANALYZER AND METHOD FOR PRODUCING THE SAME

TECHNICAL FIELD

The present invention relates to an optical analyzer for casting light into or onto a sample and for detecting a ray of light obtained from the sample in response to the cast light, such as transmitted light, reflected light, scattered light or fluorescence.

BACKGROUND ART

As a detector for a liquid chromatograph (LC), an optical analyzer is frequently used, such as an ultraviolet-visible spectrophotometer or photodiode array detector. In recent years, with the advancement and rapid spread of light-emitting diode (LED) technology, LEDs have also been used as the light source for optical analyzers. Since LEDs have a comparatively narrow peak width in its emission spectrum, they are less suitable for applications in which a wavelength scan is performed over a wide range of wavelengths. However, they can be suitably used in an optical analyzer which irradiates a sample with a specific wavelength of light, such as an absorptiometer or fluorometer. Compared to various types of conventionally and generally used light sources, LEDs have the advantage of being dramatically inexpensive while at the same time having a long life and being highly reliable.

FIG. 7 shows a schematic configuration of an absorptiometer using an LED as the light source (for example, see Patent Literature 1).

Measurement light emitted from the LED (e.g. deep ultraviolet LED) 71 serving as the light source is cast into a flow cell 72. While passing through a sample solution in the flow cell 72, the measurement light undergoes absorption in a manner that depends on the kind and amount of a component in the sample solution. The light which has undergone such an absorption enters a photodetector 73. The photodetector 73 produces a detection signal corresponding to the amount of that light. In a signal processing unit (not shown), the absorbance by the sample is calculated from the detection signal.

In order to enhance the speed and sensitivity of an analysis in an LC using such an absorptiometer as the detector, it is essential to reduce the dispersion of the sample (spread of the peak) within a passage other than the column. To this end, low-volume flow cells have been in demand. To meet such demand for low-volume cells, Patent Literature 2 discloses a technique in which a flow cell made of a silicon oxide or similar material is created by using a semiconductor manufacturing process. The use of the microfabrication technique employing the semiconductor manufacturing process enables the creation of a low-volume flow cell with a high level of dimensional precision.

Such a low-volume flow cell is intrinsically small and lightweight, thereby being convenient for reducing the size and weight of the absorptiometer. However, for high-sensitivity and high-accuracy measurements in an absorptiometer, it is necessary to manually align the optical axes of the light source and the photodetector in the process of device assembly so as to make the beam axis of the measurement light pass through a predetermined position within the flow cell. The smaller the flow cell is, the more difficult this aligning task becomes. Therefore, the device assembly requires not only a considerable amount of time and labor but also workers skilled in the assembling task. Furthermore, even if the flow cell is miniaturized, there is a limit on the size reduction of the entire device due to restrictions on the sizes of the parts in the light source and photodetector.

CITATION LIST

Patent Literature

Patent Literature 1: JP 2011-237384 A
Patent Literature 2: U.S. Pat. No. 8,213,015 B

SUMMARY OF INVENTION

Technical Problem

The present invention has been developed in view of the previously described problem. Its objective is to provide an optical analyzer which is smaller in size and lighter in weight than conventional devices, and one which requires no manual alignment of optical axes or similar tasks.

Solution to Problem

The optical analyzer according to the present invention developed for solving the previously described problem includes:

a) a base body made of a transparent or semitransparent material used as a substrate for a compound semiconductor device, oxide semiconductor device or organic semiconductor device, with a passage formed inside for allowing a sample solution to pass through;

b) a semiconductor light-emitting section formed on the surface of the base body by a semiconductor manufacturing process, for casting light into the sample solution in the passage; and c) a semiconductor light-receiving section formed on the surface of the base body by a semiconductor manufacturing process, at a position at which a ray of light obtained from the sample solution in the passage in response to the light cast from the semiconductor light-emitting section arrives.

A typical example of the transparent or semitransparent material used as the substrate for a compound semiconductor device, oxide semiconductor device or organic semiconductor device is sapphire (single crystal of aluminum oxide: $Al_2O_3$). There are also various other materials available, such as aluminum nitride (AlN), bismuth germanium oxide ($Bi_4Ge_3O_{12}$), diamond, aluminum oxide, silicon carbide, and zinc oxide.

The "transparent or semitransparent" material in the present context does not need to be transparent or translucent over a wide range of wavelengths; it only needs to be transparent or translucent to specific wavelengths (the wavelengths of the light emitted from the semiconductor light-emitting section). The material should preferably have a high refractive index.

In the optical analyzer according to the present invention, a passage having a straight tubular shape or any other appropriate shape (e.g. L-shape or U-shape) with a predetermined diameter is formed in the base body which is made of, for example, sapphire. This passage may be created by mechanical boring. It is also possible to form the passage by preparing two base bodies one or both of which have an extremely flat surface on which a groove is formed by machine work or a chemical process (e.g. etching), and bonding the two base bodies together, with the groove forming the passage inside.

An example of the semiconductor light-emitting section is an LED formed on the surface of the base body by a semiconductor manufacturing process for compound semiconductors. As a specific example, it may be created by forming a thin-film layer of gallium oxide (GaN) or similar material by crystal growth on the surface of the base body made of sapphire, and then forming an LED structure including an active layer and other portions on the gallium oxide layer. An example of the semiconductor light-receiving section is a photodiode formed on the surface of the base body made of sapphire by a semiconductor manufacturing process for compound semiconductors. This can also be created by forming a thin-film layer of gallium oxide or similar material by crystal growth on the surface of the base body, and then forming a light-receiving pn junction in the gallium oxide layer. A schottky junction type or photoconductive type light-receiving element may also be created in place of the pn junction type. The semiconductor light-emitting section and the semiconductor light-receiving sections are arranged, for example, in such a manner that they face each other across the passage in the base body orthogonally or obliquely to this passage.

When a drive current is supplied to the semiconductor light-emitting section, the semiconductor light-emitting section emits a predetermined wavelength of light into the base body. This light penetrates the transparent or semitransparent base body and is cast into the sample solution flowing through the passage inside the base body. After undergoing absorption by a component in the sample solution, the transmitted light penetrates the transparent or semitransparent base body and reaches the semiconductor light-receiving section. The semiconductor light-receiving section produces a detection signal corresponding to the amount of light which has reached it. Thus, the optical analyzer according to the present invention can obtain a detection signal which reflects the absorption by the sample solution flowing through the passage inside the base body with which the semiconductor light-emitting section and the semiconductor light-receiving section are integrated.

In general, materials used as a substrate for compound semiconductor devices, oxide semiconductor devices or organic semiconductor devices exhibit high refraction indices. Therefore, at the interface between the base body made of such a material and the air, the total reflection of light is likely to occur. Accordingly, when the light which has passed through the passage hits the interface between the base body and the air at an incident angle larger than a certain value, the light is totally reflected back into the base body. By utilizing such an effect of total reflection, it is possible to make the light traverse the passage a plurality of times before hitting the semiconductor light-receiving section. This enables a high-accuracy absorbance acquisition for a sample which has a low degree of absorption of light.

Fluorescent emission by the sample can also be detected, rather than the transmitted or scattered light, by configuring the semiconductor light-receiving section to receive light within a specific wavelength band that differs from the wavelength band of the light emitted from the semiconductor light-emitting section. That is to say, not only absorbance but also fluorescence intensity can be measured with the optical analyzer according to the present invention.

The semiconductor light-emitting section does not need to be an LED; it may also be a superluminescent diode (SLD) or laser diode (LD). The semiconductor light-receiving section may also be a phototransistor or the like, rather than the photodiode. Two or more semiconductor light-receiving sections may be provided so as to add signals obtained with those semiconductor light-emitting sections, or selectively extract one of the signals obtained with those semiconductor light-emitting sections. In the case of selectively turning on and off a plurality of semiconductor light-emitting sections, the operation may be performed in a time-divisional manner by sequentially and individually turning on and off those semiconductor light-emitting sections.

In the case of using a substrate material for organic semiconductor devices as the base body and creating the semiconductor light-emitting section and the semiconductor light-receiving section from an organic semiconductor, the semiconductor manufacturing process mentioned earlier is an organic-semiconductor manufacturing process including a solution process or the like. In other words, the semiconductor manufacturing process in the present context is a manufacturing process available for both inorganic and organic semiconductors.

Advantageous Effects of the Invention

In the optical analyzer according to the present invention, the light source, passage for allowing a flow of sample solution (i.e. flow cell), and photodetector are integrated into a single unit. Furthermore, the light source and the photodetector are created on the surface of the base body in which the passage is formed, by a semiconductor manufacturing process with a high level of positional accuracy. Accordingly, it is unnecessary to perform the manual alignment of the optical axes in the assembly process, which has been indispensable for conventional devices. A high-sensitivity measurement can be achieved without requiring such an alignment.

In the optical analyzer according to the present invention, since the gap between the light source and the flow cell, as well as the gap between the flow cell and the photodetector, are occupied by the wall surface of the passage, there is no unnecessary gap between those elements, which allows for a miniaturization of the device. Furthermore, as noted earlier, since materials used for a substrate of compound semiconductor devices, oxide semiconductor devices or organic semiconductor devices normally have high refractive indices, the total reflection is likely to occur at the interface between the base body and the air, whereby the diffusion of light within the passage is suppressed.

In the optical analyzer according to the present invention, if the passage is formed by a chemical process employing a semiconductor exposure technique, a passage having a complex form can be easily created.

Furthermore, in the optical analyzer according to the present invention, any element or circuit that can be created from a compound semiconductor, oxide semiconductor or organic semiconductor, such as a drive circuit for the semiconductor light-emitting section or an amplifier for amplifying the signal obtained with the semiconductor light-receiving section, can be mounted on the base body in which the passage is formed. Various optical elements may also be created on the same base body. For example, a lens can be created by providing a refractive-index distribution by using a refractive-index dispersion material, such as a photonic polymer. Thus, a high-functionality optical analysis unit including the functions of electrical circuits and optical systems can be provided.

BRIEF DESCRIPTION OF DRAWINGS

FIGS. 1A and 1B are schematic configuration diagrams of an optical analyzer as one embodiment of the present invention, where FIG. 1A is a sectional view at a plane containing the central line of the passage, and FIG. 1B is a sectional view at line A-A' in FIG. 1A, viewed in the arrowed direction.

FIG. 2 is a schematic configuration diagram of an optical analyzer as another embodiment of the present invention.

FIG. 3 is a schematic configuration diagram of an optical analyzer as another embodiment of the present invention.

DESCRIPTION OF EMBODIMENTS

One embodiment of the optical analyzer according to the present invention is hereinafter described with reference to the attached drawings.

FIGS. 1A and 1B are schematic configuration diagrams of the optical analyzer in the present embodiment, where FIG. 1A is a sectional view at a plane containing the central line of the passage, and FIG. 1B is a sectional view at line A-A' in FIG. 1A, viewed in the arrowed direction.

The optical analyzer 1A in the present embodiment has a base body 2 made of sapphire, which is commonly used as a material of the substrate for a compound semiconductor device. A passage 3 having a straight cylindrical tubular shape is formed inside the rectangular parallelepiped base body 2. As the base body 2, an appropriately cut piece of substrate for compound semiconductor devices can be used. The passage 3 can be bored, for example, by mechanical processing, inclusive of laser processing. To this passage 3, for example, a sample solution exiting from the exit port of the column in an LC is supplied at a substantially constant flow velocity.

In the present embodiment, sapphire is used as the material of the base body 2. However, the material is not limited to sapphire; any material is available which is used as the material of the substrate for compound semiconductor devices, oxide semiconductor devices or organic semiconductor devices, and which is transparent or semitransparent, i.e. which has the characteristics of allowing the passage of light at a predetermined wavelength or within a predetermined wavelength band. For example, aluminum nitride or bismuth germanium oxide may be used, both of which are commonly available as single crystal substrates. A diamond substrate may also be used.

On one of the two surfaces of the base body 2 which face each other across the passage 3 (in the example of FIGS. 1A and 1B, the upper and lower surfaces), an LED 4 as the semiconductor light-emitting section is formed on the base body 2. On the other one of the two surfaces, a photodiode 5 as the semiconductor light-receiving section is formed on the base body 2. Both of them are formed on the base body 2 by a standard manufacturing process for compound semiconductors.

The structure of the LED 4 and the photodiode 5 is hereinafter schematically described.

Figure 5:
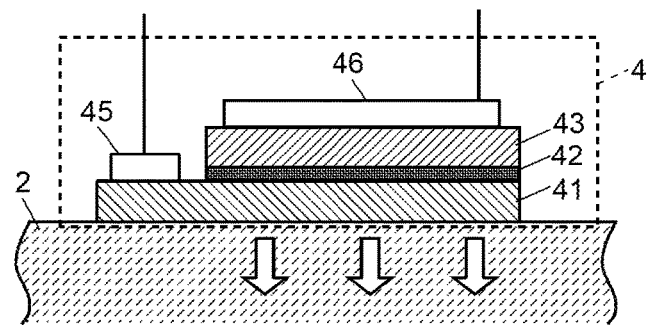
FIG. 5 is a schematic sectional view of one example of the semiconductor light-emitting section.

FIG. 5 is a schematic sectional view of one example of the LED 4.

On the surface of the base body 2, an n-type gallium nitride thin-film layer (n-GaN layer) 41 is formed by crystal growth, on which an active layer 42 is formed, which is, for example, a multilayer film of indium gallium nitride (InGaN) and gallium nitride, on which a p-type gallium nitride thin-film layer (p-GaN layer) 43 is further formed. Subsequently, the p-GaN layer 43 and the active layer 42 are partially removed. Electrodes 45 and 46 are formed on the exposed area of the n-GaN layer 41 and the p-GaN layer 43, respectively. Although not shown in FIG. 5, a protective film is formed on the entire surface of the element, and contact holes are formed in a portion of this protective film above the electrodes 45 and 46. Through these contact holes, wires are connected to the electrodes 45 and 46.

When a drive current is supplied through those wires, the active layer 42 emits light. The light is emitted on both sides, i.e. toward the external space (in FIG. 5, upward) and the base body 2 (in FIG. 5, downward). Meanwhile, the electrode 46, which covers almost the entire area of the upper surface of the p-GaN layer 43, functions as the reflective layer. The light emitted upward from the active layer 42 is reflected by this electrode 46 and changes its direction downward. Therefore, the light is efficiently emitted into the base body 2.

Figure 6:
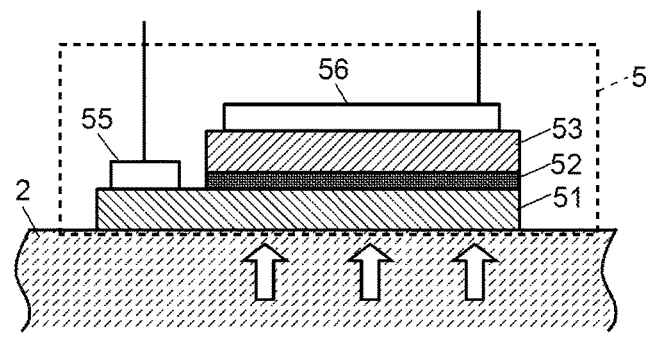
FIG. 6 is a schematic sectional view of one example of the semiconductor light-receiving section.
Figure 7:
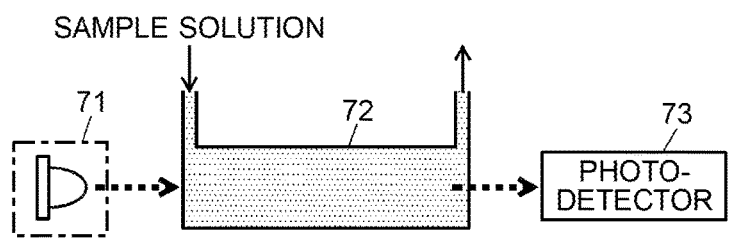
FIG. 7 is a schematic sectional view of a conventional absorptiometer.

FIG. 6 is a schematic configuration diagram of one example of the photodiode 5.

On the surface of the base body 2, for example, an n-type gallium nitride thin-film layer (n-GaN layer) 51 is formed by crystal growth. On this layer, a low-bandgap GaN-system crystal layer is formed as the light-receiving layer 52, on which a p-type gallium nitride thin-film layer (p-GaN layer) 53 is further formed, whereby a double hetero junction structure is formed. The p-GaN layer 53 and the light-receiving layer 52 are partially removed. Electrodes 55 and 56 are formed on the exposed area of the n-GaN layer 51 and the p-GaN layer 53, respectively. Although not shown in FIG. 6, a protective film is formed on the entire surface of the element, and contact holes are formed in a portion of this protective film above the electrodes 55 and 56. Through these contact holes, wires are connected to the electrodes 55 and 56.

When the light transmitted through the base body 2 reaches the light-receiving layer 52 via n-GaN layer 51, an amount of carriers corresponding to the intensity (amount) of light is generated. Those carriers move into the n-GaN layer 51 and the p-GaN layer 53. Consequently, an electric current flows through an external load via the electrodes 55 and 56. It should be noted that the electrode 56, which covers almost the entire area of the p-GaN layer 53, has the additional function of blocking the incidence of light from the external space onto the light-receiving layer 52.

As is commonly known, the structures of the LED 4 and the photodiode 5 created using compound semiconductors are not limited to the present example but can be modified in various forms. What is essential is that the LED 4 should efficiently emit light into the base body 2, while the photodiode 5 should efficiently receive the light transmitted through the base body 2 and perform the photoelectric conversion.

Returning back to FIGS. 1A and 1B for further explanations, the LED 4 and the photodiode 5 in the embodiment shown in FIGS. 1A and 1B are positioned so that the beam axis of the light emitted from the LED 4 and entering the photodiode 5 becomes substantially orthogonal to the passage 3. Therefore, the light emitted from the LED 4 and transmitted through the base body 2 travels through the sample solution in the passage 3 along a diameter of the passage 3. After undergoing absorption by the sample solution during its travel, the light further passes through the base body 2 and reaches the photodiode 5, which produces a detection signal corresponding to the amount of light it has received. In practice, the LED 4 has a certain area the entirety of which emits light, and the photodiode 5 also has a light-receiving surface having a certain area. Accordingly, along with the light orthogonal to the passage 3, some rays of light which obliquely travel at certain angles also reach the photodiode 5. However, this causes no problem for absorbance calculation since there is no temporal change in those optical paths.

As described thus far, in the optical analyzer according to the present embodiment, the LED 4 as the light source and the photodiode 5 as the photodetector are integrated with the base body 2 in which the passage 3 is formed. The LED 4 and the photodiode 5 are both created on the base body 2 with a high level of positional accuracy by a semiconductor manufacturing process. Therefore, it is unnecessary to perform the cumbersome optical-axis alignment as in the conventional devices. Furthermore, since the spaces between the LED 4 and the passage 3 as well as between the photodiode 5 and the passage 3 are occupied by the base body 2 with no unnecessary gap in between, the entire device is extremely small in size, making it possible to realize a small-size, lightweight device.

As is commonly known, in order to improve the accuracy or sensitivity for absorbance, it is preferable to increase the optical path length in the sample solution. Accordingly, instead of the arrangement as shown in FIGS. 1A and 1B in which the LED 4 and the photodiode 5 are located at positions which face each other across the passage 3 along a diameter of this passage, the LED 4 and the photodiode 5 may be arranged at positions displaced from each other in the longitudinal direction of the passage 3, as shown in FIG. 2 or 3. In the optical analyzer 1B shown in FIG. 2, among the rays of light emitted from the LED 4 into the base body 2, a ray of light obliquely emitted at a predetermined angle θ reaches the photodiode 5 after passing through the sample solution in the passage 3. The optical path length through the sample solution in the present case is longer than in the configuration shown in FIGS. 1A and 1B. There are also rays of light emitted from the LED 4 at smaller angles than θ. Those rays are not reflected at the interface between the base body 2 and the air, but are released through the base body 2 to the outside.

In the case of the optical analyzer 1C shown in FIG. 3, among the rays of light emitted from the LED 4 into the base body 2, those which hit the interface between the base body 2 and the air at angles larger than a predetermined angle are reflected at that interface. Accordingly, a ray of light which has passed through the base body 2 after being reflected two or more times at the interface between the base body 2 and the air arrives at the photodiode 5. This light traverses the sample solution in the passage 3 multiple times and travels an accordingly long optical path. At the interface between the photodiode 5 and the base body 2, the reflection conditions differ from those at the interface between the base body 2 and the air. Therefore, the light which has arrived at the position of the photodiode 5 is not reflected at this interface, but penetrates into and is detected by the photodiode 5. This, the optical path length in the sample solution can be increased by appropriately determining the positions of the LED 4 and the photodetector 5.

In the examples shown in FIGS. 1A-3, the passage 3 has a straight tubular shape. Actually, the passage 3 can be shaped in various forms. For example, the optical analyzer 1D shown in FIGS. 4A and 4B has a U-shaped passage 3. The LED 4 and the photodetector 5 are located at both ends of the central straight portion of the U-shaped passage 3, facing each other along the longitudinal direction of this portion. According to this configuration, the optical path in the sample solution has a simple straight form, which yet has a considerable optical path length and can improve the accuracy or sensitivity for absorbance.

Figure 4A:
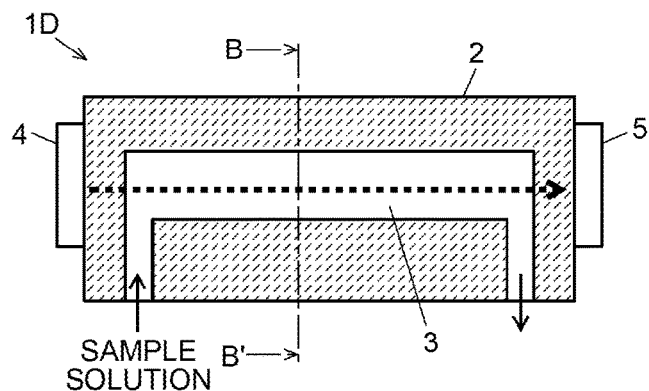
FIGS. 4A and 4B are schematic configuration diagrams of an optical analyzer as another embodiment of the present invention.
Figure 4B:
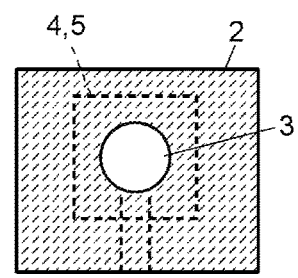

A passage 3 having a shape as shown in FIGS. 4A and 4B cannot be easily created by simple machine work. A possible method for creating such a complex-shaped passage is to prepare two base bodies with a groove formed on the surface of one or both of them by machine work or a chemical process (e.g. etching), and bond the two base bodies together, with the groove inside.

In the previous embodiment, the LED 4 and the photodiode 5 are formed on the base body 2 made of sapphire (or the like). In place of the LED 4, a different type of semiconductor light-emitting section may be formed, e.g. a superluminescent diode or laser diode. Similarly, in place of the photodiode 5, a different type of semiconductor light-receiving section may be formed, such as a phototransistor. Furthermore, not only the semiconductor light-receiving section and the semiconductor light-receiving section, but also another element or circuit which can be created by a manufacturing process for compound semiconductors may additionally be formed on the base body 2. For example, a drive circuit for supplying a drive current to the LED 4 (e.g. a current source and its control circuit), an amplifier for amplifying the signal detected with the photodiode 5, or other elements may be mounted on the base body 2. A lens or similar optical element can also be provided on the base body 2.

The number of photodiodes does not always need to be one; it is possible to provide two or more photodiodes at appropriate positions, and add the signals obtained with those photodiodes to obtain a single detection signal, or selectively extract one of the signals obtained with those photodiodes as the detection signal.

The optical analyzer according to the present invention may also be configured to detect fluorescent emission from a sample. In this case, the light emitted from the LED 4 can be used as the excitation light, along with a photodiode capable of selectively detecting light within the wavelength band of the fluorescent emission from the sample excited by the excitation light.

It is naturally possible to create the light source and the photodetector using an organic semiconductor instead of using compound semiconductors or oxide semiconductors which are more commonly used.

It should also be noted that the previous embodiments are mere examples of the present invention, and any change, modification or addition appropriately made within the spirit of the present invention will evidently fall within the scope of claims of the present application.

REFERENCE SIGNS LIST 1A, 1B, 1C, 1D . . . Optical Analyzer
2 . . . Base Body
3 . . . Passage
4 . . . LED
41, 51 . . . n-GaN Layer
42 . . . Active Layer
43, 53 . . . p-GaN Layer
45, 46, 55, 56 . . . Electrode
5 . . . Photodiode
52 . . . Light-Receiving Layer

The invention claimed is:

1. An optical analyzer comprising:
   a) a base body made of a transparent or semitransparent material used as a substrate for a compound semiconductor device, oxide semiconductor device or organic semiconductor device, with a passage formed inside for allowing a sample solution to pass through;
   b) a semiconductor light-emitting section integrally formed on and directly contacting an outer surface of the base body with the passage formed inside the semiconductor light-emitting section being configured to cast light through the base body into the sample solution in the passage; and
   c) a semiconductor light-receiving section integrally formed on and directly contacting the outer surface of the base body, at a position where a ray of light obtained from the sample solution in the passage in response to the light cast from the semiconductor light-emitting section arrives through the base body, the semiconductor light-receiving section being configured to produce a detection signal corresponding to an amount of the ray of light.

2. The optical analyzer according to claim 1, wherein:
   the semiconductor light-emitting section includes: a first n-type gallium nitride thin-film layer formed on the outer surface of the base body, an active layer which is a multilayer film of indium gallium nitride and gallium nitride formed on a top surface of the first n-type gallium nitride thin-film layer, a first p-type gallium nitride thin-film layer formed on a top surface of the active layer, a first electrode formed on the top surface of the first n-type gallium nitride thin-film layer, and a second electrode formed on a top surface of the first p-type gallium nitride thin-film layer; and
   the semiconductor light-receiving section includes: a second n-type gallium nitride thin-film layer formed on the outer surface of the base body, a light-receiving layer which is a low-bandgap gallium nitride system crystal layer formed on a top surface of the second n-type gallium nitride thin-film layer, a second p-type gallium nitride thin-film layer formed on a top surface of the light-receiving layer, a third electrode formed on the top surface of the second n-type gallium nitride thin-film layer, and a fourth electrode formed on a top surface of the second p-type gallium nitride thin-film layer.

3. The optical analyzer according to claim 1, wherein:
   the passage has a straight tubular shape; and
   the semiconductor light-emitting section and the semiconductor light-receiving section are placed on two sides facing each other across an axis of the passage and at positions displaced from each other in a longitudinal direction of the passage.

4. The optical analyzer according to claim 1, wherein the base body is made of a material selected from the group consisting of sapphire, aluminum nitride, bismuth germanium oxide, diamond, aluminum oxide, silicon carbide, and zinc oxide.

5. A method for producing an optical analyzer including a base body made of a transparent or semitransparent material used as a substrate for a compound semiconductor device, oxide semiconductor device or organic semiconductor device, with a passage formed inside for allowing a sample solution to pass through, the method comprising:
   a first process in which a semiconductor light-emitting section configured to cast light through the base body into the sample solution in the passage is formed by a semiconductor process on an outer surface of the base body with the passage formed inside such that the semiconductor light-emitting section directly contacts the outer surface of the base body; and
   a second process in which a semiconductor light-receiving section, configured to produce a detection signal corresponding to an amount of a ray of light obtained from light from the sample solution in the passage in response to the light cast from the semiconductor light-emitting section, is formed by a semiconductor process on the outer surface of the base body and at a position where the ray of light arrives through the base body such that the semiconductor light-receiving section directly contacts the outer surface of the base body.

6. The method for producing an optical analyzer according to claim 5, wherein:
   the first process includes: forming a first n-type gallium nitride thin-film layer on the outer surface of the base body, forming an active layer which is a multilayer film of indium gallium nitride and gallium nitride on a top surface of the first n-type gallium nitride thin-film layer, forming a first p-type gallium nitride thin-film layer on a top surface of the active layer, forming a first electrode on the top surface of the first n-type gallium nitride thin-film layer, and forming a second electrode on a top surface of the first p-type gallium nitride thin-film layer; and
   the second process includes: forming a second n-type gallium nitride thin-film layer on the outer surface of the base body, forming a light-receiving layer which is a low-bandgap gallium nitride system crystal layer on a top surface of the second n-type gallium nitride thin-film layer, forming a second p-type gallium nitride thin-film layer on a top surface of the light-receiving layer, forming a third electrode on the top surface of the second n-type gallium nitride thin-film layer, and forming a fourth electrode on a top surface of the second p-type gallium nitride thin-film layer.

* * * * *